United States Patent
Klein et al.

(10) Patent No.: US 6,627,761 B2
(45) Date of Patent: Sep. 30, 2003

(54) MULTIFUNCTIONAL CARBONATES AND DERIVATIVES

(75) Inventors: Howard P. Klein, Austin, TX (US); David C. Alexander, Austin, TX (US); Susan A. Woodrum, Round Rock, TX (US); James R. Machac, Jr., Lago Vista, TX (US)

(73) Assignee: Huntsman Petrochemical Corporation, Austin, TX (US)

( * ) Notice: Subject to any disclaimer, the term of this patent is extended or adjusted under 35 U.S.C. 154(b) by 0 days.

(21) Appl. No.: 09/822,914

(22) Filed: Mar. 30, 2001

(65) Prior Publication Data

US 2002/0183474 A1 Dec. 5, 2002

(51) Int. Cl.$^7$ ............................................. C07D 317/10
(52) U.S. Cl. ..................................................... 549/229
(58) Field of Search .......................................... 549/229

(56) References Cited

U.S. PATENT DOCUMENTS

| | | |
|---|---|---|
| 3,072,613 A | 1/1963 | Whelan et al. |
| 5,175,231 A | 12/1992 | Rappoport et al. |
| 5,340,889 A | 8/1994 | Crawford et al. |
| 5,703,136 A | 12/1997 | Gillis et al. |
| 5,763,622 A * | 6/1998 | Podszun et al. ............ 549/229 |
| 5,855,961 A | 1/1999 | Hoenel et al. |
| 6,120,905 A | 9/2000 | Figovsky |

FOREIGN PATENT DOCUMENTS

WO    WO 98/58004    12/1998

* cited by examiner

*Primary Examiner*—Joseph K. McKane
*Assistant Examiner*—Ebenezer Sackey
(74) *Attorney, Agent, or Firm*—Gardere Wynne Sewell LLP

(57) ABSTRACT

The present invention provides a more economical method of producing multifunctional carbonate resins. It overcomes the disadvantage of using relatively expensive starting material, such as polyglycidyl ethers, that have traditionally been used. The present invention makes use of readily available and inexpensive multi-isocyanate compounds reacted with organic carbonates that contain pendant hydroxyl groups to produce products that contain two or more carbonate functionalities. One form of the present invention is a method for preparing a carbonate urethane compound by reacting a carbonate containing compound that also contains a reactive hydroxyl group with a compound containing at least two isocyanate groups. The reaction is performed in a solvent and in the presence of a base.

9 Claims, No Drawings

MULTIFUNCTIONAL CARBONATES AND DERIVATIVES

FIELD OF THE INVENTION

This invention relates generally to the field of chemical synthesis, and more particularly to methods and compositions for the preparation of multifunctional carbonates, curing agents prepared from them, and epoxy formulations prepared with the curing agents.

BACKGROUND OF THE INVENTION

Multifunctional carbonates are useful chemical compounds that can be used directly, or as intermediates in the preparation of other materials. They can be used to prepare polyurethanes, polyurethane polyureas, polyamide polyurethane polyols, polyether polyurethane polyols, polycarbonate polyurethane polyols, and curing agents for epoxy resins.

Multifunctional carbonate compounds have traditionally been formed using polyglycidyl ethers as starting materials. While this is an effective method of producing the desired compounds, the polyglycidyl ethers are relatively expensive materials, which can make some applications of the resulting products economically disadvantageous.

There is a need for a method of producing multifunctional carbonates, for such downstream uses as forming polyurethanes and epoxy curing agents, which makes use of relatively inexpensive and readily available starting materials.

BRIEF SUMMARY OF THE INVENTION

The present invention provides a more economical method of producing multifunctional carbonate resins. It overcomes the disadvantage of using relatively expensive starting materials, such as polyglycidyl ethers, that have traditionally been used.

One form of the present invention is a method for preparing a carbonate urethane compound by reacting a carbonate containing compound that also contains a reactive hydroxyl group with a compound containing at least two isocyanate groups. The reaction is performed in a solvent and in the presence of a base.

Another form of the present invention is a composition for a curing agent that is a compound containing two or more first carbamate linkages, where each first carbamate linkage is connected to a second carbamate linkage. The ester side of the first carbamate linkages are connected to the ester side of corresponding second carbamate linkages. In addition, there is a terminal amine group connected to the amido side of the second carbamate linkages.

DETAILED DESCRIPTION

Although this description discloses the making and using of various embodiments of the present invention, these specific embodiments are merely illustrative of a specific way to make or use the present invention, and are in no way meant to limit it. The present invention provides many applicable inventive concepts that can be embodied in a wide variety of specific contexts.

The present invention makes use of readily available and inexpensive multi-isocyanate compounds reacted with organic carbonates that contain pendant hydroxyl groups to produce products that contain two or more carbonate functionalities. These compounds, that contain two or more carbonate groups, are defined for the purposes of this application as "multifunctional carbonates." The preparation of the multifunctional carbonates of the present invention is done without the need for the formulator to directly handle an isocyanate compound in order to make a curing agent.

The multifunctional carbonates of the present invention can be further modified by reaction with diamines to produce compounds containing a multiplicity of carbamate linkages, and having terminal amine groups.

The present invention is capable of producing compounds that provide advantages in the curing of epoxy resins. Derivatives produced by the methods of the present invention react more quickly with epoxy resins than examples prepared by methods in the prior art. In addition, the cured epoxies produced have superior toughness and adhesion properties over those produced by previously disclosed methods.

One form of the present invention is a method for preparing a carbonate urethane compound by reacting a carbonate containing compound that also contains a reactive hydroxyl group with a compound containing at least two isocyanate groups. The reaction is performed in a solvent and in the presence of a base.

Another form of the present invention is a composition for a curing agent that is a compound containing two or more first carbamate linkages, where each first carbamate linkage is connected to a second carbamate linkage. The ester side of the first carbamate linkages are connected to the ester side of corresponding second carbamate linkages. In addition, there is a terminal amine group connected to the amido side of the second carbamate linkages.

Yet another form of the present invention is a method for preparing a curing agent by reacting a compound containing at least two carbamate linkages, where each carbamate linkage is connected to at least one carbonate, with an excess of a diamine. The reaction is performed in a solvent. A carbamate linkage, as referred to in this application, with the ester and amido sides labeled is shown below.

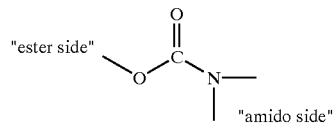

Another form of the present invention is a method of curing an epoxy resin by reacting the resin with a curing agent having one of the general structures:

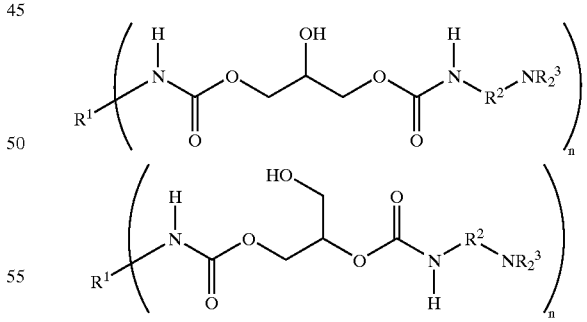

where $R^1$ is an alkyl or aryl unit, $R^2$ is a spacer chain of two to two hundred atoms in length, $R^3$ is independently hydrogen or an alkyl, aryl or polyether segment, and n=2 or 3. The term "spacer unit" refers to a chain of atoms that may be straight or branched. The length of the spacer chain is defined in terms of the number of atoms in the backbone of the spacer chain that connects the two units in question. A nonlimiting example of a six atom spacer chain would be a hexamethylene chain, as shown below.

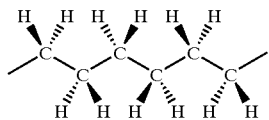

Yet another form of the present invention is the reaction product of an epoxy resin and a curing agent, where the curing agent is a compound containing two or more first carbamate linkages, where each first carbamate linkage is connected to a second carbamate linkage. The ester side of the first carbamate linkages are connected to the ester side of corresponding second carbamate linkages. In addition, there is a terminal amine group connected to the amido side of the second carbamate linkages.

The isocyanate containing compounds used in the present invention can be essentially any alkyl, aryl or mixed alkyl and aryl compound that contains two or more isocyanate groups. These compounds include, but are not limited to, 1,3 phenylene diisocyanate; 1,4 phenylene diisocyanate, 1,4 diisocyantobutane; 1,6 diisocyanatohexane, 1,8-diisocyanatooctane; 2,4,6 trimethyl-1,3phenylene diisocyanate; 3,3'-4,4'biphenylene diisocyanate; trans-1,4-cyclohexylene diisocyanate; α-4-tolylene diisocyanate; isophorone diisocyanate; m-xylylene diisocyanate; methylene di-p-phenyl diisocyanate; toluene 2,4 disocyanate; toluene 2,6 diisocyanate.

The diamines used in some of the embodiments of the present invention can be essentially any alkyl, aryl or mixed alkyl and aryl diamine. Examples include, but are not limited to; 1,3 diaminopropane; 1,4 diaminobutane; 1,6 diaminohexane; 1,2 diaminobenzene; 1,3 diaminobenzene; 1,4 diaminobenzene; 2,3 diaminotoluene; 2,4 diaminotoluene; diaminoxylene; ethylenediamine; diethylene triamine, triethylenetetramine.

Essentially any commercially available epoxy resin may be used in the embodiments of the present invention that require one. Non-limiting examples of epoxy resins that are appropriate for use in the present invention include EPON 828® (Shell/Resolution Polymers), Epotuf 37-140® (Reichhold), DER 331® (Dow), GY-6010® (Vantico).

For the embodiments of the present invention that employ a solvent, the solvent may be a pure solvent or a mixture. Any solvent that at least partially dissolves the reactants and does not react with the reactants may be used. The choice of an appropriate solvent will be apparent to one of ordinary skill in the art.

EXAMPLE 1

Preparation of a Bis(Carbonate-Urethane)of Toluene Diisocyanate

To a one-liter, round bottom 3-necked flask, fitted with a mechanical stirrer, thermometer and dropping funnel, was added 118 g of glycerin carbonate (I) (1.0 moles) and 200 ml. of dry tetrahydofuran (THF). After addition of 1.0 g dimethylcyclohexylamine (DMCHA), the resulting solution was stirred under nitrogen at ambient temperature. Then, 87 g (1.0 equiv.) of Rubinate® 80/20 (Huntsman Corp.) toluenediisocyanate (TDI) (II) was then added dropwise while controlling the exothermic reaction so that the temperature did not exceed 60° C. After the addition of compound II was complete the reaction product was maintained at 50° C. for one hour. The resulting product was primarily a solution of III in THF, a light yellow mobile liquid. The reaction is shown diagrammatically below.

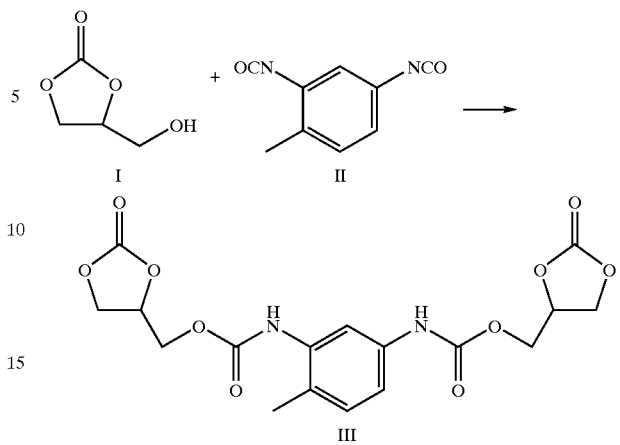

EXAMPLE 2

Preparation of a Bis(Carbonate-Urethane) of Isophorone Diisocyanate

To the apparatus described in Example 1 was added 127 g (1.0 mole) of 93% glycerin carbonate, I, and 200 ml of dry THF. After the addition of 1.0 g of dimethylcyclohexylamine, the resulting solution was stirred under nitrogen at ambient temperature while 111 g (1.0 equivalents) of isophorone diisocyanate VI was added dropwise at a rate such that the temperature of the reaction never exceeded 60° C. After the addition was complete the reaction was maintained at 50 to 65° C. for around two hours. The product is a water white solution. The reaction is shown diagrammatically below.

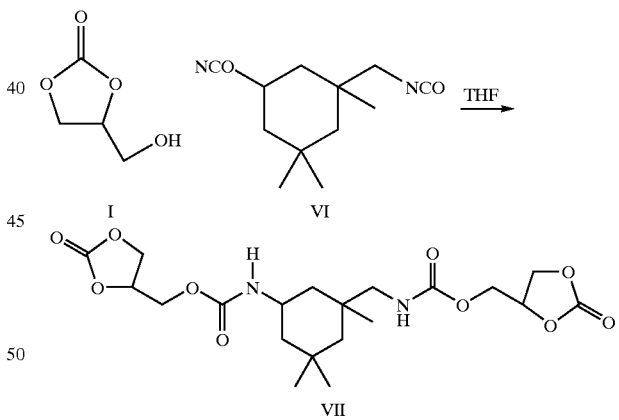

EXAMPLE 3

Preparation of an Amine Terminated Epoxy Curing Agent

To the same apparatus as described in Example 1 was added 500 g (3.38 moles) of XTJ-504 (Huntsman Corp.) (i.e. triethyleneglycol diamine) IV which was stirred at ambient temperature, while the reaction mixture from Example 1 was added slowly from the dropping funnel so as to control the reaction and keep the temperature below 60° C. Finally, the reaction mixture was digested at 50–60° C. for about one hour. The resulting light yellow solution was then rotary evaporated to remove the THF. The final product was a light-yellow, mobile liquid with the following analysis:

| Total Acetylatables | 10.03 meq./g. |
|---|---|
| Total Amine | 8.09 meq./g. |

The product is a mixture of 50% IV and 50% V by weight. The amine hydrogen equivalent weight for the product is 61.

The reaction is shown diagrammatically below

III
+

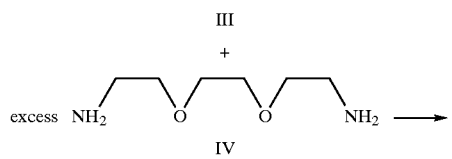

excess NH$_2$       IV       NH$_2$ →

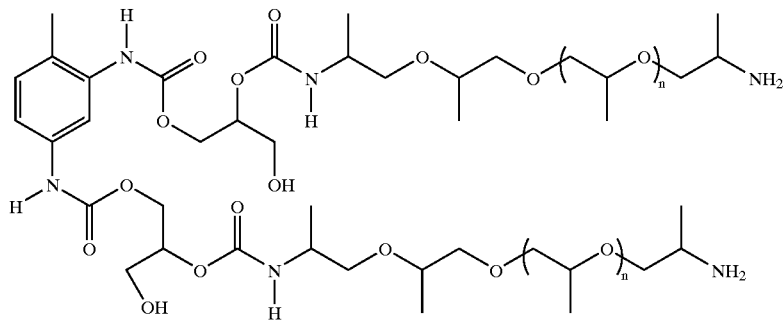

230 terminated product VI.
n = 1,2

VI

-continued

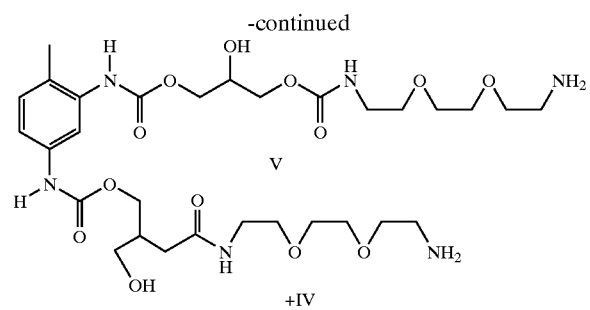

V

+IV

EXAMPLE 4

Comparative Example

To the apparatus described in Example 1 was added 195 g (1.32 mole) of XTJ-504 (IV), that was heated under a nitrogen atmosphere to 60° C. Then, 235 g (0.34 equivalents) of XTC-84 (Huntsman Corp.), a triglycidyl ether carbonate of equivalent weight 691, was added dropwise over a 15-minute period. The reaction mixture was slightly exothermic and the temperature increased to about 75° C. during the addition, after which time it was digested for one hour at 80° C. The resulting product was a mobile, light-yellow liquid with amine odor.

| Analysis: | Viscosity, cps 25° C. = | 254 |
|---|---|---|
| | Total Acetylatables, meq/g. = | 6.24 |
| | Total Amine, meq/g. = | 5.18 |
| | Amine Hydrogen Equiv. Weight = | 94 |

EXAMPLE 5

Example 3 was repeated, except that the THF solution of III was added to 665 (~2.90 moles) of JEFFAMINE® D-230 (Huntsman Corp.). After digestion and removal of the THF with a rotary evaporator, the resulting product was a viscous yellow liquid that was a mixture of approximately 50% JEFFAMINE® D-230 (Huntsman Corp.)and 50% of the JEFFAMINE® D-230 terminated product VI.

| Analysis: | TOTAL AMINE, meq./g. = | 5.028 |
|---|---|---|
| | Amine Hydrogen Eqiv. Wt. = | 94 |

EXAMPLE 6

To the apparatus described in Example 1 was added 263 g (1.78 moles) of XTJ-504 IV that was stirred at room temperature while 120 g of VII from Example 2 in 100 ml of THF was added dropwise so that the temperature never exceeded 60° C. After the addition was complete the reaction was maintained at 50° C. to 62° C. for between one and two hours. The resulting clear solution was evaporated to remove the THF. The product VIII, as a mixture of isomers, was 380 grams of a mobile water-white liquid with a total amine content of 7.684 equivalents per gram. The reaction is shown diagrammatically below.

VII + 4 IV →

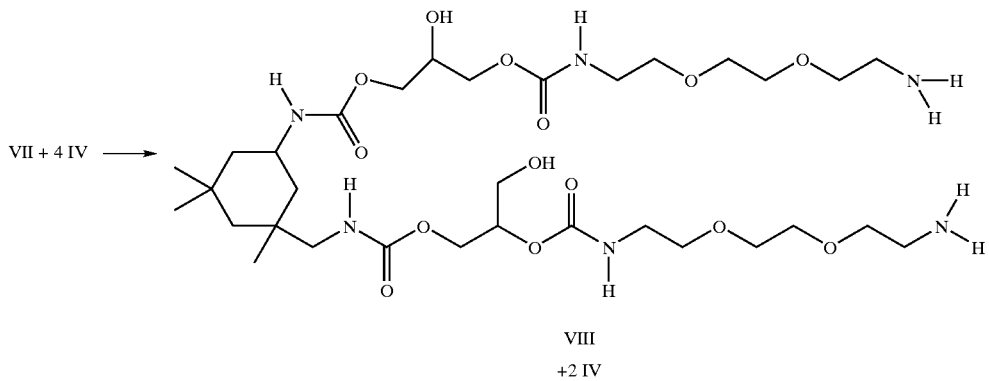

VIII
+2 IV

EXAMPLES 7–10

| Example | 7 | 8 | 9 | 10 |
|---|---|---|---|---|
| Epon 828 | 100 parts | 100 parts | 100 parts | 100 parts |
| Product of Example 4 | 53 parts | | | |
| Product of Example 3 | | 32 parts | | |
| Product of Example 5 | | | 53 parts | |
| Product of Example 6 | | | | 35 parts |
| $T_g$, DSC, °C. | 58 | 77 | 83 | 87 |
| $T_{max}$, DSC, °C. | 114 | 101 | 113 | 103 |
| gel time, min | 73 | 30 | 73 | 41 |
| viscosity, cps | 2100 | 3800 | 12000 | 5000 |
| Max. exotherm, °C. | 179 | 206 | 156 | 218 |

The products of Examples 7–10 were mixed with the epoxy resin EPON 828 in the ratios shown in the table. The formulation shown in Example 8 cured about twice as fast as that shown in Example 7, which used the curing agent prepared by a method disclosed in the prior art. Examples 9 and 10 show results of two additional curing agents prepared by the present invention.

What is claimed is:

1. A method for preparing a carbonate urethane compound comprising reacting:
   glycerin carbonate; with
   a compound containing at least two isocyanate groups; and
   a base; in
   a solvent.

2. The method recited in claim 1, wherein the isocyanate-containing compound comprises an alkyl isocyanate.

3. The method recited in claim 1, wherein the isocyanate-containing compound comprises an aryl isocyanate.

4. The method recited in claim 1, wherein the isocyanate-containing compound comprises 2,4 diisocyantotoluene.

5. The method recited in claim 1, wherein the solvent comprises an ether.

6. The method recited in claim 1, wherein the solvent comprises tetrahydofuran.

7. The method recited in claim 1, wherein the base comprises an amine.

8. The method recited in claim 1, wherein the base comprises dimethylcyclohexylamine.

9. A method for preparing a carbonate methane compound comprising reacting:
   glycerin carbonate; with
   2,4 diisocyantotoluene; and
   a base; in
   a solvent.

* * * * *